(12) United States Patent
Weil et al.

(10) Patent No.: US 7,160,538 B2
(45) Date of Patent: Jan. 9, 2007

(54) SUSPENSION AEROSOL FORMULATIONS OF PHARMACEUTICAL PRODUCTS

(75) Inventors: Hans-Hermann Weil, Gau-Bickelheim (DE); Ottfried Daab, Ingelheim (DE)

(73) Assignee: Boehringer Ingelheim KG (DE)

( * ) Notice: Subject to any disclaimer, the term of this patent is extended or adjusted under 35 U.S.C. 154(b) by 270 days.

(21) Appl. No.: 10/934,611

(22) Filed: Sep. 3, 2004

(65) Prior Publication Data

US 2005/0031548 A1 Feb. 10, 2005

Related U.S. Application Data

(60) Continuation of application No. 10/638,987, filed on Aug. 12, 2003, now abandoned, which is a continuation of application No. 10/072,400, filed on Feb. 6, 2002, now abandoned, which is a division of application No. 09/525,431, filed on Mar. 14, 2000, now Pat. No. 6,419,899, which is a continuation of application No. 08/990,252, filed on Dec. 15, 1997, now abandoned, which is a continuation of application No. 08/597,230, filed on Feb. 6, 1996, now abandoned, which is a continuation of application No. 08/282,402, filed on Jul. 28, 1994, now abandoned, which is a continuation of application No. 07/910,353, filed on Oct. 1, 1992, now abandoned.

(51) Int. Cl.
*A61K 9/12* (2006.01)
*A61K 9/14* (2006.01)

(52) U.S. Cl. ............................ 424/45; 424/46; 424/489

(58) Field of Classification Search ................ 424/45, 424/46, 489
See application file for complete search history.

(56) References Cited

U.S. PATENT DOCUMENTS

| | | | |
|---|---|---|---|
| 2,490,764 A | 12/1949 | Benning et al. |
| 3,014,844 A | 12/1961 | Thiel et al. |
| 3,095,355 A | 6/1963 | Abramson |
| 3,219,533 A | 11/1965 | Mullins |
| 4,044,126 A | 8/1977 | Cook et al. |
| 4,174,295 A | 11/1979 | Bargigia et al. |
| 4,352,789 A | 10/1982 | Thiel |
| 4,810,488 A | 3/1989 | Jinks |
| 4,814,161 A | 3/1989 | Jinks et al. |
| 5,118,494 A | 6/1992 | Schultz et al. |
| 5,182,097 A | 1/1993 | Byron et al. |
| 5,605,674 A | 2/1997 | Purewal et al. |
| 5,653,962 A | 8/1997 | Akehurst et al. |
| 5,674,471 A | 10/1997 | Akehurst et al. |
| 5,695,743 A | 12/1997 | Purewal et al. |
| 5,891,420 A | 4/1999 | Cutie |
| 6,149,892 A | 11/2000 | Britto |
| 6,153,173 A | 11/2000 | Sapsford et al. |

FOREIGN PATENT DOCUMENTS

| | | |
|---|---|---|
| CA | 2075058 | 8/1991 |
| DE | 1542076 | 3/1970 |
| DE | 1719443 | 4/1972 |
| DE | 27 03 119 | 8/1977 |
| DE | 3903336 | 8/1990 |
| DE | 40 03 270 | 8/1991 |
| EP | 315783 | 5/1987 |
| EP | 0 247 608 | 12/1987 |
| EP | 0 384 371 | 8/1990 |
| EP | 0 504 112 | 9/1992 |
| EP | 0 550 031 | 7/1993 |
| EP | 0653205 | 5/1995 |
| EP | 0656 206 | 6/1995 |
| GB | 837465 | 1/1958 |
| GB | 902590 | 8/1962 |
| GB | 2 001 334 | 1/1979 |
| GB | 2046093 | 11/1980 |
| GB | 2 125 426 | 3/1984 |
| JP | 55131096 | 11/1980 |
| JP | 022 72084 | 4/1989 |
| WO | WO 86/03750 | 7/1986 |
| WO | WO 86/04233 | 7/1986 |
| WO | WO 91/11173 | 8/1991 |
| WO | WO 91/11496 | 8/1991 |
| WO | WO 92/22288 | 12/1992 |
| WO | WO 96/19198 | 6/1996 |
| WO | WO 98/34595 | 8/1998 |

OTHER PUBLICATIONS

Du Pont: Fluorocarbon/Ozone: Alternatives to Fully Halogenated Chlorofluorocarbons: The Du Pont Development Program; Mar. 1987.
Research Disclosure, May 1989, Kenneth Mason Publications Ltd., ISSN 0374-4353.
F.X. Fischer et al. "CFC Propellant Substitution: International Perspectives," Pharm. Technol.Inc., Sep. 1989, pp. 44, 46, 50, 52.
L. Lachman et al., "The Theory of Practice of Industrial Pharmacy," Philadelphia, Ch. 20, p. 590 and 603-604, 1986.
Hoeschst Press Release #7252, "Hoechst: Development of Alternatives to Fully Halogenated CFC's Takes Priority" Oct. 25, 1989.

(Continued)

*Primary Examiner*—Johann Richter
*Assistant Examiner*—Mina Haghighatian
(74) *Attorney, Agent, or Firm*—Mary-Ellen M. Devlin; Michael P. Morris; Alan R. Stempel

(57) ABSTRACT

Pharmaceutical preparations for producing powder aerosols using propellant gases which use TG 227, and possibly also TG 11, TG 12, TGH 114, propane, butane, pentane or DME.

1 Claim, No Drawings

OTHER PUBLICATIONS

J.Wesley Clayton, Jr., Ph.D. Fluorocarbon Toxicity: Past, Present, Future; J. Soc. Cosmetic Chemists, vol. 18, pp. 333-350, May 27, 1967.

The Condensed Chemical Dictionary, 5th printing, 1965, State College, PA. p. 26.

O-A Neumueller, Rompps Chemie-Lexikon, 8, Aufl, 1987, vol. 5, pp. 3931.

A. Oberholz, Frankfurter Allgemeine Zeitung, Oct. 25, 1989, p. 7, "Fur den Schutz des Lebens auf der Erde;" EnglishTranslation "For Preservation of Life on Earth."

Respiratory Drug Delivery, editor, Peter R. Byron, based on a symposium held May 1988 at the Univ. of Kentucky, P. R. Byron editor, RM161.R448, 1990 CRC Press, Inc., Library of Congress #89-2401; pp. 40-43 and 250.

Proceedings of the Workshop on High Temperature Heat Pumps, Hannover, Nov. 1989; pp. 60-66.

P.A. Sanders, Handbook of Aerosol Technology, 2nd Edition, 1979, Chapter 21, pp. 400-411.

Helskel (Hoeschst), Hepafluorpropan in pharmazeutischen Aerosolen, notiz ueber elnen besuch bel der firma Boehringer Ingelheim KG Apr. 29, 1987.

Noelken (Hoechst), Toxikologische Entwicklung von FKW 227 Gespraechsnotiz (memo) Boehringer Ingelhelm KG.

DIN Safety Data Sheet, Hoechst AG, Jan. 25, 1988.

Blick auf Hoechst: HP 029, Nr. 8, Dec. 1989.

Hoechst zum Ersatz von FCKW, Stand: Sep. 1990.

Karl Thoma, Aerosole: Moeglichkeiten und Probleme einer Darreichungsform, Werbe und Vertriebsgesellschaft Deutscher Apotheker m.b.H., Frankfurt am Main, 1979 pp. 153-161.

F. Moren et al.; Aerosols in Medicine Principles, Diagnosis and Theraphy, Elsevier, 1985, pp. 261-278.

Respiratory Drug Delivery, editor, Peter R. Byron, based on a symposium held May 1988 at the Univ. of Kentucky, P. R. Byron editor, RM161.R448, 1990 CRC Press, Inc., Library of Congress #89-24018; pp. 168-186.

F. Moren, AB Draco, "Dosage Forms and Formulations for Drug Administration to the Respiratory Tract" Drug Development and Industrial Pharmacy, 1987, 13 p. 704.

Chemical Business New Bulletin, vol. 19, Dec. 1, 1989.

Remington's Pharmaceutical Sciences, 13th Edition, Mack Publishing, Easton, PA, 1965 Chapter 42, pp. 661-662.

A.T. Florence & D. Attwood, Physicochemical Principles of Pharmacy, 1981, Macmillian Press.

IMS Health—Midas Feb. 25, 2000, "Aerosol Usage in Germany" pp. 1 and 2.

The Merck Index, 11th Edition, 1989.

The Science and Technology of Aerosol Packaging, Sciarra and Stoller, John Wiley & Sons, 1974; pp. 435-450.

T. S. Johnson and H. Deger of Hoechst Celanese Corp., "Specialty fluoroaliphatic chemicals," a paper presented at Chemspec USA 1989, pp. 61-63, a symposium highlighting innovation, manufacture and applications of specialty chemicals held Oct. 10-11, 1989.

Transcript of Faxes: The European Agency for the Evaluation of Medicinal Products, Human Medicines Evaluation Unit, London Sep. 13, 1995, CPMP/503/95.

Abstract to Hoechst Marion Roussel Pharmaceuticals, Respiratory Drug Delivery V, Program Proc., 5th (1996).

Auszug aus der Beilstein-Datenbank (Abstract of the Beilstein-Databank).

Hoechst High Chem Magazin 16/1994, p. 42.

J.J. Sciarra & A.J. Cutie: The Theory and Practice of Industrial Pharmacy; Pharmaceutical Aerosols-chapter 20, pp. 589-618; Supplied by the British Library.

Auszug Rote Liste, 1989, Praeparate der Firma Hoechst.

Priority Document for WO 91/11173 and PCT/GB 91/00133 dated Feb. 2, 1990.

Physician's Desk Reference Germany (Rote Liste/Fachinformation) Ailergospasmin N, VIATRIS Gmbh & Co. KG Intal, Aarane N (Aventis Pharma).

Physician's Desk Reference Germany (Rote Liste/Fachinformation) Apaflurane (Copyright 2004 American Chemical Society.

WHO Drug Information Vo. 16, No. 4, 2002.

Solkane(R) 227 pharma and 134a Pharma (NEW)—Datasheet.

Remington's 17th Edition, Pharmaceutical Sciences, 1985.

Physician's Desk Reference, 43rd Edition 1989.

List of Some Suspension Products for Oral Inhalation.

SUSPENSION AEROSOL FORMULATIONS OF PHARMACEUTICAL PRODUCTS

The invention relates to new propellent gases which contain as a typical ingredient 1,1,1,2,3,3,3-heptafluoropropane (TG 227), the use of these propellent gases in pharmaceutical preparations suitable for producing aerosols, and these pharmaceutical preparations themselves.

Aerosols of powdered (micronised) drugs are used widely in therapy, e.g. in the treatment of obstructive diseases of the respiratory tract. If such aerosols are not produced by atomising the pharmaceutical powder or by spraying solutions, suspensions of the drugs in liquefied propellent gases are used. The latter consist primarily of mixtures of TG 11 (trichlorofluoromethane), TG 12 (dichlorodifluoromethane) and TG 114 (1,2-dichloro-1,1,2,2-tetrafluoroethane), optionally with the addition of lower alkanes such as butane or pentane, or with the addition of DME (dimethylether). Mixtures of this kind are known for example from German Patent 1178975.

Owing to their harmful effect on the earth's atmosphere (destruction of the ozone layer, Greenhouse effect) the use of chlorofluorocarbons has become a problem, with the result that the search is on for other propellent gases or propellent gas mixtures which do not have the above-mentioned harmful effects or, at least, have them to a lesser degree.

However, this search has come up against major problems, since propellent gases for therapeutic use have to satisfy numerous criteria which cannot easily be reconciled, e.g. in terms of toxicity, stability, vapour pressure, density and solubility characteristics.

As has now been found, TG 227 (1,1,1,2,3,3,3-heptafluoropropane, optionally in admixture with one of more propellent gases from the group comprising TG 11 (trichlorofluoromethane), TG 12 (dichlorodifluoromethane), TG 114 (1,2-dichloro-1,1,2,2-tetrafluoroethane), propane, butane, pentane and DME (dimethylether) is particularly suitable for use in therapeutic preparations.

The compounds to be used in addition to TG 227 are added if the properties of the propellent gas are to be modified, e.g. if the liquefied propellent gas is to have a different density, different pressure or different solubility characteristics. Pharmaceutical preparations based on the propellent gas contain an active substance in finely divided form, usually as a suspension, and generally also contain surface-active substances, e.g. a phospholipid (such as lecithin), an ester of a polyalcohol (such as sorbitol) with higher saturated or unsaturated fatty acids (e.g. stearic, palmitic or oleic acid), such as sorbitan trioleate, or a polyethoxysorbitan ester of a higher, preferably unsaturated fatty acid. The adjuvant may be present in the mixture in dissolved or undissolved form. In some cases, the suspensions produced with the new propellent gas have a tendency to separate out. However, it has been found that the separated suspensions can easily be uniformly distributed again in the suspension medium simply by shaking.

The ratios of quantities of the individual ingredients of the propellent gas mixture may be varied within wide limits. The proportion (in percent by weight) is 10 to 100% in the case of TG 227. The mixture may also contain up to 50% propane and/or butane and/or pentane and/or DME and/or TG 11 and/or TG 12 and/or TG 114. Within the limits specified the ingredients are chosen to add up to 100%. Propellent gas mixtures which contain 30 to 100% TG 227 are preferred.

The proportion of suspended drug in the finished preparation is between 0.001 and 5%, preferably between 0.005 and 3%, more particularly between 0.01 and 2%. The surface-active substances are added in amounts of from 0.01 to 10%, preferably 0.05 to 5%, more particularly 0.1 to 3% (here, as in the case of the pharmaceutical substances, the percentage by weight of the finished preparation is given). The pharmaceutical substances used in the new preparations may be any of the substances suitable for use by inhalation or possibly for intranasal administration. They include, therefore, in particular betamimetics, anticholinergics, steroids, antiallergics, PAF-antagonists and combinations of these active substances.

The following are given as specific examples:

Examples of betamimetics

Bambuterol
Bitolterol
Carbuterol
Clenbuterol
Fenoterol
Hexoprenalin
Ibuterol
Pirbuterol
Procaterol
Reproterol
Salbutamol
Salmeterol
Sulfonterol
Terbutalin
Tulobuterol
1-(2-fluoro-4-hydroxyphenyl)-2-[4-(1-benzimidazolyl)-2-methyl-2-butylamino]ethanol
erythro-5'-hydroxy-8'-(1-hydroxy-2-isopropylaminobutyl)-2H-1,4-benzoxazin-3-(4H)-one
1-(4-amino-3-chloro-5-trifluoromethylphenyl)-2-tert.-butylamino)ethanol
1-(4-ethoxycarbonylamino-3-cyano-5-fluorophenyl)-2-(tert.-butylamino)ethanol.

Examples of anticholinergics

Ipratropium bromide
Oxitropium bromide
Trospium chloride
Benzilic acid-N-β-fluoroethylnortropine ester methobromide

Examples of steroids

Budesonide
Beclomethasone (or the 17, 21-dipropionate thereof)
Dexamethason-21-isonicotinate
Flunisolide

Examples of antiallergics

Disodium cromoglycate
Nedocromil

Examples of PAF-antagonists 4-(2-Chlorophenyl)-9-methyl-2-[3-(4-morpholinyl)-3-propanon-1-yl]-6H-thieno[3.2-f][1.2.4]triazolo[4.3-a][1.4]diazepine.
3-(Morpholin-4-yl-carbonyl)-5-(2-chlorphenyl)-10-methyl-7H-cyclopental[4.5]thieno-[3.2-f][1.2.4]triazolo[4.3-a][1.4]diazepine 3-(Di-n-propylamincarbonyl)-5-(2-chlorphenyl)-10-methyl-7H-cyclopental[4.5]thieno-[3.2-f ][1.2.4]triazolo[4.3-a][1.4]diazepine The active substances may also be combined, e.g., betamimetics plus anticholinergics or betamimetics plus anti-allergics.

Examples of preparations according to the invention (amounts given in percent by weight):

1) 0.10% Oxitropium bromide
   0.01% Soya lecithin
   4.0% Pentane
   95.89% TG 227

2) 0.3% Fenoterol
   0.1% Soyalecithin
   10.0% Pentane
   70.0% TG 227
   19.6% TG 134a 3) 0.1% Ipratropium bromide
   0.1% Soya lecithin
   20.0% Pentane
   20.0% Butane
   49.8% TG 11

4) 0.3% Fenoterol
   0.1% Soya lecithin
   30.0% TG 11
   69.6% TG 227

5) 1.5% Disodium cromoglicate
   0.1% Tween 20

6) 0.3% Salbutamol
   0.2% Span 85

98.4% TG 227
   1.4% Butane 7) 0.15% Fenoterol
   0.06% Ipratropium-bromide
   0.10% Soya lecithin
   40.00% TG 11
   19.69% Propane
   40.00% TG 227

20.0% Pentane
   60.0% TG 227
   19.5% TG 12

8) 0.1% Ipratropium-bromide
   0.1% Soya lecithin
   15.3% Propane
   30.5% TG 11
   54.0% TG 227

The invention claimed is:

1. In a pharmaceutical formulation for administration of micronized or powdered drug to the respiratory tract of a warm-blooded animal via inhalation wherein propellant gases are employed, the improvement comprising employing 1,1,1,2,3,3,3-heptafluoropropane as the sole propellant gas.

* * * * *